United States Patent [19]

Tsuchiya et al.

[11] Patent Number: 5,677,326

[45] Date of Patent: Oct. 14, 1997

[54] INDOLINE COMPOUND AND 5-HT$_3$ RECEPTOR ANTAGONIST CONTAINING THE SAME AS ACTIVE INGREDIENT

[75] Inventors: Shinji Tsuchiya; Nobuyuki Yasuda; Atsushi Fukuzaki; Koichi Kazama, all of Tokyo, Japan

[73] Assignee: Tokyo Tanabe Company Limited, Tokyo, Japan

[21] Appl. No.: 624,417

[22] PCT Filed: Sep. 30, 1994

[86] PCT No.: PCT/JP94/01641

§ 371 Date: Mar. 29, 1996

§ 102(e) Date: Mar. 29, 1996

[87] PCT Pub. No.: WO95/09168

PCT Pub. Date: Apr. 6, 1995

[30] Foreign Application Priority Data

Sep. 30, 1993 [JP] Japan ................... 5-245778
Mar. 31, 1994 [JP] Japan ................... 6-062728

[51] Int. Cl.$^6$ .................. A61K 31/415; C07D 403/06
[52] U.S. Cl. .................. 514/394; 514/396; 548/304.7; 548/305.1; 548/305.4; 548/305.7; 548/306.1
[58] Field of Search ................... 548/305.1, 306.1, 548/305.4, 304.7, 305.7; 514/394, 396

[56] References Cited

U.S. PATENT DOCUMENTS

| | | | |
|---|---|---|---|
| 3,401,173 | 9/1968 | Chow et al. | 548/304.7 |
| 3,772,315 | 11/1973 | Regel et al. | 548/309.4 X |
| 4,820,757 | 4/1989 | Spang et al. | 548/305.1 X |
| 5,344,927 | 9/1994 | Ohta et al. | 544/31 |

FOREIGN PATENT DOCUMENTS

| | | | |
|---|---|---|---|
| 0 381 422 | 8/1990 | European Pat. Off. | 544/31 |
| 52-12162 | 1/1977 | Japan | 548/305.1 |
| 3-223278 | 10/1991 | Japan | 544/31 |
| 0786266 | 5/1982 | U.S.S.R. | 548/309.4 |

OTHER PUBLICATIONS

The Journal of Pharmacology and Experimental Therapeutics vol. 261, No. 1, 297 (1992) Keiji Miyata et al.
British Journal of Pharmacology, 100, 497 (1990) Helen E. Moss & Gareth J. Sanger.
British Journal of Pharmacology, 112 (Proceedings Supplement), 101P, (1994). "Effects of Dexamethasone on Endothelin–1 Release and Growth of Rat Aortic Smooth Muscle Cells".

Croatica Chemica Act 45, 297–312 (1973) I. Butula.

*Primary Examiner*—Floyd D. Higel
*Attorney, Agent, or Firm*—Griffin, Butler, Whisenhunt & Kurtossy

[57] ABSTRACT

Indoline compounds represented by the general formula:

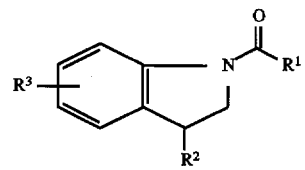

wherein $R^1$ represents the group

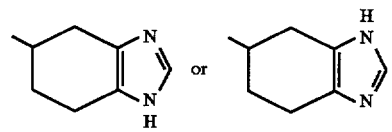

$R^2$ represents a phenyl group which may be substituted or an aromatic heterocyclic group, and $R^3$ represents hydrogen, a halogen, or a lower alkyl group, hydroxyl group, lower alkoxy group, carbamoyl group or lower alkoxycarbonyl group, and physiologically acceptable salts thereof, and their solvates, as well as 5-HT$_3$ receptor antagonists containing them as effective components. The indoline compounds of the invention have stronger antagonism against intestinal 5-HT$_3$ receptors than known 5-HT$_3$ receptor antagonists and also have excellent sustained action, making them useful as prophylactic or therapeutic agents against vomiting or irritancy induced by chemotherapy or radiation, irritable bowel syndrome, diarrhea, and the like.

28 Claims, 1 Drawing Sheet

INDOLINE COMPOUND AND 5-HT₃ RECEPTOR ANTAGONIST CONTAINING THE SAME AS ACTIVE INGREDIENT

FIELD OF THE ART

The present invention relates to indoline compound which is useful as drug, and specifically as 5-$HT_3$ receptor antagonist.

BACKGROUND OF THE ART

The 5-$HT_3$ receptor, which is one of the 5-hydroxytryptamine (5-HT, generic name: serotonin) receptors, is widely distributed throughout the sensory nervous system, the autonomic nervous system and the central nervous system, and the action of 5-HT on their receptors is said to cause gastrointestinal motor disturbances, irritant moods, vomiting, algesia, bradycardia, and to have nervous activity affecting feelings, appetite, memory, etc. Consequently, drug agents with 5-$HT_3$ receptor antagonism are reported to be effective for the treatment and prevention of the irritant mood, vomiting, accompanying cancer chemotherapy, migraine, arrhythmia, and nervous disorders including schizophrenia, mania, etc., as well as diarrhea, irritable bowel syndrome, increased urinary frequency and dysuria.

Among such drug agents with 5-$HT_3$ receptor antagonism, there are used 4-amino-5-chloro-N-[2-(diethylamino)ethyl]-2-methoxybenzamide (generic name: "Metoclopramide"), 1,2,3,4-tetrahydro-9-methyl-3-[(2-methyl-1H-imidazol-1-yl) methyl]-4H-carbazol-4-one-hydrochloride dihydrate (GR38032F, generic name: "Ondansetron hydrochloride"), endo-8-methyl-8-azabicyclo[3,2,1]octa-3-yl indol-3-ylcarboxylate (ICS 205-930, generic name: "Tropisetron"), N-(endo-9-methyl-9-azabicyclo [3,3,1]nona-3-yl)-1-methyl-indazol-3-carboxamide hydrochloride (generic name: "Granisetron"), etc., which are used to treat vomiting elicited by antitumor agents such as cisplatin and the like, while other compounds such as (R)-(−)-5-[(1-methylindol-3-yl) carbonyl]-4,5,6,7-tetrahydrobenzimidazole hydrochloride (YM-060) are currently receiving much attention.

However, a number of subtypes of the 5-$HT_3$ receptor are reported to exist. As a result of research on a 5-$HT_3$ receptor in the intestine, it is believed that this intestinal 5-$HT_3$ receptor plays a role in various forms of diarrhea, for example stress-related diarrhea and secretory diarrhea caused by cholera and other bacteria, and thus compounds with strong antagonism for the intestinal 5-HT3 receptor are expected to work as antidiarrheal drugs. It has in fact been reported that the above mentioned 5-$HT_3$ receptor antagonists Ondansetron, Granisetron, YM-060, etc. suppress stress-related diarrhea in animal models, with the effect of YM-060 being the strongest (The Journal of Pharmacology and Experimental Therapeutics, Vol.261, No. 1, 297 (1992)). It is also believed that abdominal pain accompanying digestive system diseases such as diarrhea, irritable bowel syndrome, constipation, etc. is heightened by dilative stimulation of the intestinal tract, and indications are that 5-$HT_3$ antagonists may possibly lower sensitivity to such dilative stimulation (British Journal of Pharmacology, 100, 497 (1990) and British Journal of Pharmacology, 112 (Proceedings Supplement), 101P (1994). However, despite the abundant research on 5-$HT_3$ receptor antagonists as antiemetics, there has been a little research on 5-$HT_3$ receptor antagonists as antidiarrheal drugs, and as yet the characteristics of the intestinal 5-HT3 receptor has not been sufficiently studied.

On the other hand, since it is also known that gastric emptying is hindered by administration of antitumor agents such as cisplatin, 5-HT3 receptor antagonists are also expected to suppress these as well.

Incidentally, compounds which are structurally similar to the compounds of the present application are described in Japanese laid-open patent publication No. Hei-3-223278, but as will be explained later, these and other such compounds have low antagonism for the intestinal 5-$HT_3$ receptor and provide little alleviation of abdominal pain, while they have also proven to be inadequate in terms of duration of action and promotion of gastric emptying.

In view of the above, the present inventors have sought to develop a 5-$HT_3$ receptor antagonist which not only has the conventional use as an antiemetic but is also useful as an antidiarrheal drug, and as a result of diligent research on compounds exhibiting particularly high antagonism for the intestinal 5-$HT_3$ receptor, we have discovered indoline compounds which, compared to known compounds with similar structures and other typical 5-$HT_3$ antagonists, have strong antagonism for the intestinal 5-$HT_3$ receptor and strong antidiarrheal and abdominal pain-alleviating effects, while also having excellent duration of action and promotion of gastric emptying.

DISCLOSURE OF THE INVENTION

The present invention relates to indoline compounds (hereunder collectively referred to as "compound (a)") represented by the following general formula:

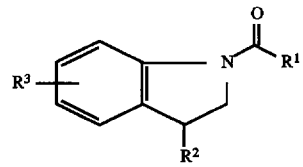

wherein $R^1$ represents the group

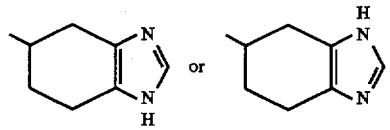

$R^2$ represents a phenyl group which may be substituted or an aromatic heterocyclic group, and $R^3$ represents hydrogen, a halogen, or a lower alkyl group, hydroxyl group, lower alkoxy group, carbamoyl group or lower alkoxycarbonyl group, and to their physiologically acceptable salts and their solvates.

When $R^2$ is a substituted phenyl group, suitable substituents may be lower alkyl groups such as methyl, ethyl, propyl and isopropyl, hydroxyl group, lower alkoxy groups such as methoxy, ethoxy, propoxy and isopropoxy, halogens such as fluorine, chlorine and bromine, an amino group, lower alkylamino groups, alkylcarbamoyl groups, carbamoyl groups, sulfamoyl groups, lower alkoxycarbonyl groups, nitro group, and acylamino groups such as acetylamino and propionylamino. Examples of aromatic heterocyclic groups for $R^2$ include monovalent groups based on thiophene, oxazole, thiazole, furan, pyran, pyrrole, imidazole, pyrazole, isothiazole, isoxazole, pyridine, pyrazine, pyrimidine, pyridazine, indole, quinoline, isoquinoline, etc. In a preferred form of compound (a), $R^2$ is a phenyl group which may be substituted, and $R^3$ is hydrogen.

As physiologically acceptable salts of compound (a) there may be mentioned salts of inorganic acids such as hydrochloric acid, hydrobromic acid, hydroiodic acid, sulfuric acid. phosphoric acid and nitric acid and salts of organic acids such as acetic acid, carbonic acid, tartaric acid, fumaric acid, maleic acid, oxalic acid, citric acid, malic acid, benzoic acid, methanesulfonic acid, ethanesulfonic acid and benzenesulfonic acid.

Compound (a) may be produced by reacting a carboxylic acid compound (hereunder referred to as "compound (b)") represented by the following general formula:

wherein $R^4$ represents the same group as $R^1$ or $R^1$ with a protective group which may be easily converted to $R^1$ by a common organic reaction, after its conversion to an acid halide, with a compound (hereunder referred to as "compound (c)") represented by the following general formula:

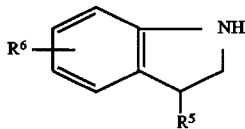

wherein $R^5$ represents the same group as $R^2$ or a group which may be easily converted to $R^2$ by a common organic reaction, and $R^6$ represents the same group as $R^3$ or a group which may be easily converted to $R^3$ by a common organic reaction, or by directly reacting compound (b) and compound (c) by, for example, the mixed anhydride method using a suitable condensing agent, protecting or deprotecting if necessary by common organic synthesis.

Optically active compound (a) may be prepared either by using optically active compound (b) and compound (c), or by differential recrystallization of a salt of the optical isomer mixture of compound (a) with an optically active acid, chromatographic separation of compound (a), or other commonly used methods for optical resolution.

Racemic compound (b) are publicly known, and may be prepared, for example, by the method described in CROATICA CHEMICA ACTA 45, 297–312 (1973), or a method based thereon.

Compound (c) may be produced by a publicly known method such as the method described in Japanese laid-open patent publication No. Sho-52-12162, or according to a publicly known method combined if necessary with protection or deprotection by common organic synthesis.

Optically active compounds (b) and (c) may be obtained by separating optically inactive compounds (b) or (c) using a common method of optical resolution.

The compounds of the present invention may be administered, for example, orally in the form of tablets, capsules, granules, powder or syrup, or parenterally in the form of an injection or suppository. Such formulations may be prepared by well-known methods, using such additives as excipients, binders, disintegrators, lubricants, stabilizers, flavor correctives, and the like. Their dosages will differ depending on the relevant symptoms, age, etc., but normally they may be administered to adults at a dosage of 0.01 μg-1 mg/kg body weight per day, either once a day or in divided doses.

BEST MODE FOR EMBODYING THE INVENTION

REFERENCE EXAMPLE 1

Figure 1:
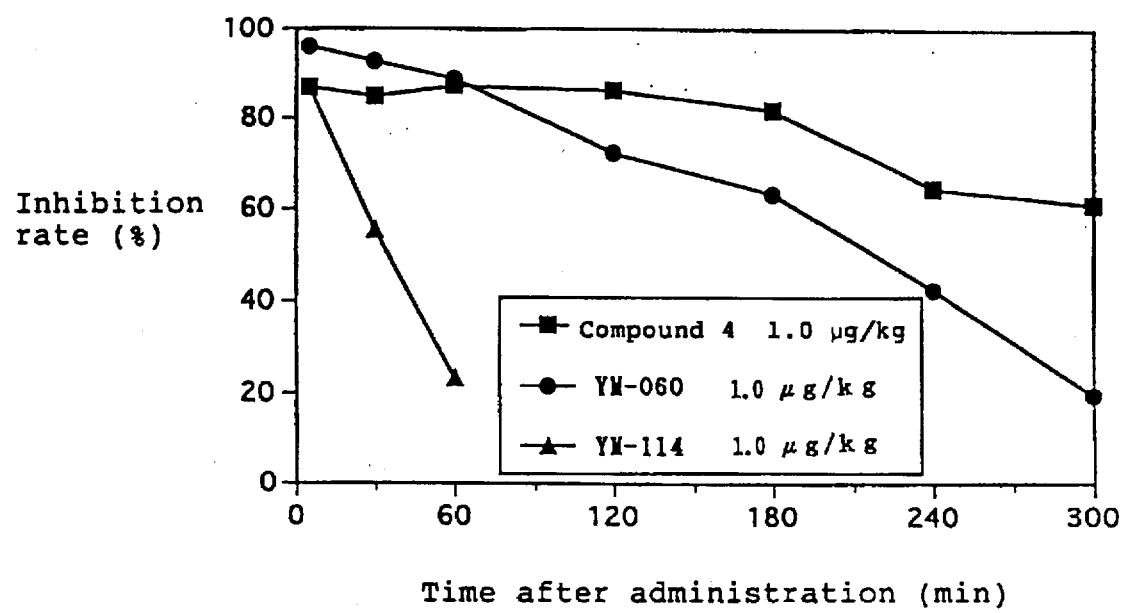
FIG. 1 is a graph relating to Experiment 7, showing the results of testing the prolonged BJ reflex inhibition action (relationship between inhibition rate and time lapse) of a compound of the invention and a comparison compound.

(+)-3-phenylindoline:

Six grams of 3-phenylindoline and 13.4 ml of triethylamine were dissolved and mixed in methylene chloride, and a solution of 11.0 g of N-tosyl-D-prolyl chloride in 30 ml of methylene chloride was added dropwise to the solution with stirring under ice cooling. The reaction solution was returned to room temperature, and after stirring for 2 hours it was diluted with chloroform and washed with saturated sodium bicarbonate water. The chloroform layer was dried and concentrated to obtain an oily residue. The oily residue was a mixture of two optical isomers, and these two optical isomers were observed separately on TLC (TLC plate, $60F_{254}$ silica gel, product of Merck Co,. developing solvent: toluene: ethyl acetate =5:1).

Toluene was added to the above mentioned oily residue, and the precipitated white crystals were collected by filtration. The crystals were recrystallized with ethyl acetate and filtered to obtain 5.06 g of crystals which had a lower Rf on above mentioned TLC, and that was one of the optical isomers of 3-phenyl-1-(N-tosyl-D-prolyl)-indoline.

$^1$H-NMR (δ ppm, $CDCl_3$, 270 MHz): 1.8~2.0 (1H, m), 2.0~2.3 (3H, m), 2.40 (3H, s), 3.4~3.6 (2H, m), 4.28 (1H, dd), 4.52 (1H, t), 4.6~4.8 (2H, m), 6.9~7.1 (2H, m), 7.2~7.4 (8H, m), 7.74 (2H, d), 8.22 (1H, d)

A 5.0 g portion of the 3-phenyl-1-(N-tosyl-D-prolyl)-indoline obtained above was suspended in a mixed solution of 40 ml acetic acid and 15 ml concentrated hydrochloric acid, and heated under reflux for 6 hours. The reaction solution was concentrated under reduced pressure and washed with toluene, and then the aqueous layer was made basic with an aqueous sodium hydroxide solution and extracted with diethyl ether. The extract was dried and concentrated to obtain 1.52 g of (+)-3-phenylindoline as yellow crystals.

$^1$H-NMR (δ ppm, $CDCl_3$, 270 MHz): 3.5 (1H, brs), 3.50 (1H, t), 3.93 (1H, t), 4.49 (1H, t), 6.6~6.8 (2H, m), 6.91 (1H, d), 7.07 (1H, t), 7.2~7.4 (5H, m)

$[\alpha]_D$=+52.3° (c=0.26, MeOH)

REFERENCE EXAMPLE 2

(+)-4,5,6,7-tetrahydrobenzimidazole-5-carboxylic acid hydrochloride:

An 84 g portion of ethyl 4,5,6,7-tetrahydrobenzimidazole-5-carboxylate was dissolved in 350 ml of 6N hydrochloric acid and heated under reflux for 2 hours. The reaction solution was concentrated under reduced pressure, and 200 ml of acetone was added to the residue and the precipitated crystals were collected by filtration and dried to obtain 69 g of 4,5,6,7-tetrahydrobenzimidazole-5-carboxylic acid hydro-chloride. A 54 g portion of this 4,5,6,7-tetrahydrobenzimidazole-5-carboxylic acid hydrochloride was mixed in 75 ml of thionyl chloride and heated under reflux for one hour. The reaction solution was concentrated, and the resultant mixture was added with stirring under ice cooling to 500 ml of a chloroform solution which contained 50 g indoline and 38 ml triethylamine. After stirring the mixture at room temperature overnight, it was washed with 300 ml of a 2N aqueous sodium hydroxide solution and then dried and concentrated. Ethyl acetate was added to the residue to precipitate crystals which were collected by filtration to obtain 71 g of 5-(2,3-dihydroindol-1-yl) carbonyl-4,5,6,7-tetrahydrobenzimidazole.

A 70 g portion of this 5-(2,3-dihydroindol-1-yl) carbonyl-4,5,6,7- tetrahydrobenzimidazole was dissolved in 2.2 l MeOH at 50° C., and this was mixed with a solution of 47 g of (+)-dibenzoyltartaric acid in 2.2 l MeOH at 50° C. The mixture was allowed to stand at room temperature overnight, and then the precipitated crystals were collected by filtration. The crystals were added to 200 ml of 4N hydrochloric acid and thoroughly stirred, and the mixture was washed with ether to remove the insoluble precipitate. The aqueous layer was made alkaline with an aqueous sodium hydroxide solution, and the precipitate was extracted with a mixed solvent of chloroform and ethanol (4:1). The extract was dried and concentrated, and an oily residue was obtained. This residue was dissolved in 300 ml MeOH and then mixed with a solution of 40 g (+)-dibenzoyltartaric acid in 800 ml MeOH. The mixture was allowed to stand at room temperature overnight, and then the precipitated crystals were collected by filtration. The crystals were added to 200 ml of 4N hydrochloric acid and thoroughly stirred, and the precipitated insoluble portion was removed with ether. The aqueous layer was made alkaline with an aqueous sodium hydroxide solution, and the precipitate was extracted with a mixed solvent of chloroform and ethanol (4:1). The extract was dried and concentrated the extract to obtain 24 g of (−)-5-(2,3-dihydroindol-1-yl)carbonyl-4,5,6,7-tetrahydrobenzimidazole as a white powder. Specific rotation of the white powder:

[α]$_D$=−18° (c=0.25, MeOH)

A 24 g portion of the above mentioned (−)-5-(2,3-dihydroindol-1-yl)carbonyl-4,5,6,7-tetrahydrobenzimidazole was dissolved in 120 ml of 6N hydrochloric acid and heated under reflux for 3 hours. The reaction solution was evaporated to dryness under reduced pressure to obtain a residue which was then dissolved in water, made alkaline with an aqueous sodium hydroxide solution, and washed with ethyl ether. Subsequent acidification of the aqueous layer with hydrochloric acid and concentration under reduced pressure yielded a white powder of (+)-4,5,6,7-tetrahydrobenzimidazole-5-carboxylic acid hydrochloride containing NaCl.

The optical rotation of this aqueous hydrochloride solution was (+).

REFERENCE EXAMPLE 3

3-(3-methoxyphenyl)indoline:

Ninety grams of m-anisaldehyde, 250 g of (methoxymethyl)triphenylphosphonium chloride and 800 ml of tetrahydrofuran were mixed, and then 82.5 g of potassium tert-butoxide was added to this mixed suspension under ice-cooling, and the solution was stirred for 2 hours at room temperature. The reaction solution was poured in ice water, and after distilling out the THF, the mixture was extracted with ethyl acetate. The extract solution was washed with sodium bicarbonate aqueous solution and dried. The extract solution was concentrated to obtain a residue to which hexane was then added, and the resulting precipitate was filtered out. The filtrate was then concentrated, and the residue was subjected to silica gel column chromatography. Elution was then performed with a mixed solvent of hexane:ethyl acetate=20:1, to obtain 90 g of methyl (3-methoxystyryl) ether.

A 90 g portion of the abovementioned methyl (3-methoxystyryl) ether was dissolved in 100 ml of ethanol. Then the solution was added dropwise to a mixed solution of 59.3 g phenylhydrazine, 800 ml ethanol and 53 ml concentrated hydrochloric acid under reflux, and after the addition, reflux heating was continued for 2 more hours. The reaction mixture was then cooled to room temperature, and after adding water, sodium chloride and a small amount of ethyl acetate, the mixture was stirred and the precipitated crystals were collected by filtration. The crystals were dissolved in chloroform and washed with dilute hydrochloric acid and sodium bicarbonate aqueous solution. And the solution was dried and concentrated to obtain a residue. Then toluene was added to the residue, and after refluxed for one hour. After cooling, precipitated crystals were then collected by filtration to obtain 89.6 g of 3-(3-methoxyphenyl)indole.

$^1$H-NMR (δ ppm, CDCl$_3$, 270 MHz): 3.87 (3H, s), 6.8~6.9 (1H, m), 7.1~7.3 (4H, m), 7.3~7.5 (3H, m), 7.96 (1H, d), 8.21 (1H, brs)

Ten grams of the abovementioned 3-(3-methoxyphenyl) indole, 700 ml of 6N hydrochloric acid and 300 ml of ethanol were mixed and refluxed while 100 g zinc powder was added in small portions, and then the reflux was continued for 5 hours. The reaction solution was made alkaline with an aqueous sodium hydroxide solution and extracted with chloroform. The resultant extract solution was concentrated to a residue which was then dissolved in diluted hydrochloric acid, and washed with ether. The aqueous layer was made alkaline with sodium hydroxide, extracted with chloroform, and dried and concentrated to obtain 4.9 g of 3-(3-methoxyphenyl)indoline.

$^1$H-NMR (δ ppm, CDCl$_3$, 270 MHz): 3.50 (3H, s), 3.8 (1H, br), 3.78 (3H, s), 3.93 (1H, t), 4.46 (1H, t), 6.6~7.0 (6H, m), 7.07 (1H, t), 7.2~7.3 (1H, m)

REFERENCE EXAMPLE 4

(+)-3-(3-methoxyphenyl)indoline:

The same basic procedure as in Reference Example 1 was followed, except that the 3-(3-methoxyphenyl)indoline obtained in Reference Example 3 was used instead of 3-phenylindoline, to obtain (+)-3-(3-methoxyphenyl) indoline. The $^1$H-NMR of this (+)-3-(3-methoxyphenyl) indoline was the same as the $^1$H-NMR of the 3-(3-methoxyphenyl)indoline obtained in Reference Example 3.

[α]$_D$=+59.4° (c=0.10, MeOH)

REFERENCE EXAMPLE 5

(+)-3-(3-hydroxyphenyl)indoline:

A 3.0 g portion of the (+)-3-(3-methoxyphenyl)indoline obtained in Reference Example 4 was dissolved in 30 ml of dichloromethane, and this solution was added dropwise to 40 ml of a boron tribromide dichloromethane solution (1 mole/liter) at −70° C. After stirring the solution at room temperature overnight, ice water was added, the pH was adjusted to 9 with sodium bicarbonate, and the mixture was extracted with a chloroform/ethanol mixed solvent. After drying and concentration, ether was added to the residue to precipitate crystals which were then collected by filtration to obtain 2.7 g of 3-(3-hydroxyphenyl)indoline.

$^1$H-NMR (δ ppm, CDCl$_3$, 270 MHz): 3.46 (1H, t), 3.91 (1H, t), 4.42 (1H, t), 3.5~5.0 (1H, br), 6.6~6.8 (48, m), 6.8~7.0 (2H, m), 7.0~7.3 (2H, m)

[α]$_D$=+46.4° (c=0.30, MeOH)

REFERENCE EXAMPLE 6

(+)-3-(4-hydroxyphenyl)indoline:

The same basic procedure as in Reference Example 3 was followed to obtain 3-(4-methoxyphenyl)indoline. This 3-(4-methoxyphenyl)indoline was used according to the same basic procedure as in Reference Example 1 to obtain (+)-3-(4-methoxyphenyl)indoline.

$[\alpha]_D$=+40.6° (c=0.28, MeOH)

The (+)-3-(4-methoxyphenyl)indoline was used according to the same basic procedure as in Reference Example 5 to obtain the (+)-3-(4-hydroxyphenyl)indoline listed in the above heading.

$^1$H-NMR (δ ppm, CDCl$_3$, 270 MHz): 1.5~2.5 (1H, br), 3.45 (1H, t), 3.91 (1H, t), 4.44 (1H, t), 6.6~6.8 (4H, m) 6.91 (1H, dd), 7.0~7.2 (3H, m)

$[\alpha]_D$=+32.1° (c=0.37, MeOH)

REFERENCE EXAMPLE 7

Optically active 3-(2-hydroxyphenyl)indoline:

The same basic procedure as in Reference Example 3 was followed to obtain 3-(2-methoxyphenyl)indoline. This 3-(2-methoxyphenyl)indoline was used according to the same basic procedure as in Reference Example 1 to obtain (−)-3-(2-methoxyphenyl)indoline.

$[\alpha]_D$=−32.3° (c=0.30, MeOH)

The (−)-3-(2-methoxyphenyl)indoline was used according to the same basic procedure as in Reference Example 5 to obtain the optically active 3-(2-hydroxyphenyl)indoline listed in the above heading. $^1$H-NMR (δ ppm, CDCl$_3$, 270 MHz): 3.65 (1H, dd), 3.86 (1H, t), 4.49 (1H, dd), 6.7~6.9 (4H, m), 7.0~7.3 (4H, m)

REFERENCE EXAMPLE 8

(+)-4,5,6,7-tetrahydrohenzimidazole-5-carboxylic acid hydrochloride

Methyl benzimidazole-5-carboxylate was subjected to catalytic reduction according to the method described in CROATICA CHEMICA ACTA 45, 297-312 (1973), to obtain methyl 4,5,6,7-tetrahydrobenzimidazole-5-carboxylate. Using this methyl 4,5,6,7-tetrahydrobenzimidazole-5-carboxylate in the same manner as in Reference Example 2 yielded a white powder of (+)-4,5,6,7-tetrahydrobenzimidazole-5-carboxylic acid hydrochloride containing NaCl.

A 1.2 g portion of the NaCl-containing (+)-4,5,6,7-tetrahydrobenzimidazole-5-carboxylic acid hydrochloride white powder was mixed with 2 ml of thionyl chloride and refluxed for one hour. The excess thionyl chloride in the reaction solution was removed by distillation, and 3 ml of ethanol was added to the residue which was then allowed to stand overnight. Sodium bicarbonate aqueous solution was added to the ethanol solution to make it weakly basic, and the solution was extracted with a chloroform/ethanol mixed solution. The organic layer was dried and concentrated to obtain 0.55 g of ethyl (+)-4,5,6,7-tetrahydrobenzimidazole-5-carboxylate exhibiting the specific rotation indicated below.

$[\alpha]_D$=+39.5° (c=0.99, MeOH)

$^1$H-NMR (δ ppm, CDCl$_3$, 270 MHz): 1.28 (3H, t), 1.85~2.05 (1H, m), 2.15~2.30 (1H, m), 2.55~2.95 (5H, m), 4.17 (2H, q), 4.1~4.4 (1H, brs), 7.55 (1H, s) mp: 113.8°~114.4° C.

A 0.3 g portion of this ethyl (+)-4.5,6,7-tetrahydrobenzimidazole-5-carboxylate was dissolved in 2 ml of 6N hydrochloric acid and refluxed for 1.5 hours, and then evaporated to dryness under reduced pressure to obtain 4,5,6,7-tetrahydrobenzimidazole-5-carboxylic acid hydrochloride with the optical rotation indicated below. mp: 245°–248° C.

$[\alpha]_D$=+15.8° (c=1.25, MeOH)

$^1$H-NMR (δ ppm, D$_2$O, 270 MHz): 2.00~2.20 (1H, m), 2.20~2.40 (1H, m), 2.70~3.15 (5H, m), 8.52 (1H, s)

REFERENCE EXAMPLE 9

5-hydroxy-3-phenylindoline (racemic modification) and 7-hydroxy-3-phenylindoline (racemic modification) were synthesized in the same manner as in Reference Example 5, 3-(4-fluorophenyl)indoline (racemic modification), 3-(3-fluorophenyl)indoline (racemic modification), 7-fluoro-3-phenylindoline (racemic modification) and 5-fluoro-3-phenylindoline (racemic modification) were synthesized in the same manner as in Reference Example 3, and 3-(4-fluorophenyl) indoline (optically active compound) and 3-(3-fluorophenyl)indoline (optically active compound) were synthesized in the same manner as in Reference Example 1.

PREFERRED EMBODIMENT 1

5-[(3-phenylindolin-1-yl)carbonyl]-4,5,6,7-tetrahydrobenziamidazole (compound 1):

A mixture of 440 mg 4,5,6,7-tetrahydrobenzimidazole-5-carboxylic acid hydrochloride (racemic modification) and 3 ml thionyl chloride was refluxed for 30 minutes. The reaction solution was concentrated under reduced pressure and the resultant residue was dissolved in 3 ml of chloroform. To this solution was added 0.2 g of 3-phenylindoline (racemic modification) dissolved in 2 ml of chloroform, and 0.42 ml of triethylamine, with stirring under ice cooling. After returning the solution to room temperature and stirring for 2 hours, saturated sodium bicarbonate aqueous solution was added, the mixture was extracted with chloroform. The extract solution was dried and concentrated to obtain a white residue. This residue was purified by silica gel column chromatography to obtain 200 mg of 5-[(3-phenylindolin-1-yl)carbonyl]-4,5,6,7-tetrahydrobenziamidazole (compound 1) as a mixture of 4 optical isomers.

$^1$H-NMR (δ ppm, CDCl$_3$, 270 MHz): 2.0~2.3 (2H, m), 2.5~3.2 (5H, m), 4.0~4.1 (1H, m), 4.5~4.7 (2H, m) 6.9~7.1 (2H, m), 7.14~7.4 (6H, m), 7.49 (0.5H, s), 7.51 (0.5H, s), 8.34 (1H, d)

HPLC (column: CHIRALCEL OD 4.6Φ×50 mm, product of Dicell Chemical Industries, KK., elution solvent: n-hexane: isopropyl alcohol=6:1, flow rate: 0.8 ml/min). Retention times: 9.43 min, 10.97 min, 19.24 min, 33.96 min.

PREFERRED EMBODIMENT 2

5- [(3-phenylindolin-1-yl)carbonyl ]-4,5,6,7-tetrahydrobenzimidazole hydrochloride (compound 2):

A 100 mg portion of the 5-[(3-phenylindolin-1-yl) carbonyl]-4,5,6,7-tetrahydrobenzimidazole produced in the preferred embodiment 1 was dissolved in 3 ml ethanol, and 0.4 ml of 4N hydrogen chloride solution in ethyl acetate was added under ice cooling. The solution was concentrated under reduced pressure to obtain a partially oily residue. After adding 5 ml of ethyl acetate thereto and stirring, the insoluble portion was collected by filtration to obtain the 5-[(3-phenylindolin-1-yl)carbonyl]-4,5,6,7-tetrahydrobenziamidazole hydrochloride (compound 2) listed in the above heading.

$^1$H-NMR (δ ppm, DMSO-d$_6$, 270 MHz): 1.9~1.9 (1H, m), 2.0~2.3 (1H, am), 2.6~3.0 (4H, am), 3.0~3.2 (1H, m), 4.0~4.2 (1H, m), 4.6~4.8 (2H, m), 6.8~7.1 (2H, am), 7.1~7.4 (6H, m), 8.19 (1H, d), 8.88 (0.5H, s), 8.90 (0.5H, s), 14.3 (2H, brs)

PREFERRED EMBODIMENT 3

5-[(3-phenylindolin-1-yl)carbonyl]-4,5,6,7-tetrahydrobenziamidazole (compound 3):

A mixture of white powder containing 11 g of (+)-4,5,6,7-tetrahydrobenzimidazo le-5-carboxylic acid hydrochloride obtained in Reference Example 2 and 80 ml of thionyl chloride was refluxed for 2 hours. The reaction solution was concentrated under reduced pressure and the resultant residue was dissolved in 200 ml of chloroform. A 7.9 g portion of the (+)-3-phenylindoline produced in Reference Example 1 was dissolved in 50 ml of chloroform and added to the above mentioned chloroform solution with stirring under ice cooling. A solution of 8.2 ml triethylamine in 20 ml of chloroform was then added dropwise to the reaction solution over 2 hours. After returning the solution to room temperature and stirring for 2 hours, saturated sodium bicarbonate aqueous solution was added, the mixture was extracted with chloroform. The extract solution was dried and concentrated to obtain a white residue. Ethyl acetate was added to the residue to precipitate crystals which were then collected by filtration and recrystallized twice from a mixed solvent of chloroform and ethyl acetate to obtain 12 g of the 5-[(3-phenylindolin-1-yl)carbonyl]-4,5,6,7-tetrahydrobenzimidazole (compound 3) listed in the above heading.

$^1$H-NMR (δ ppm, CDCl$_3$, 270 MHz): 1.9~2.2 (2H, m), 2.5~3.2 (5H, m), 4.0~4.1 (1H, m), 4.5~4.7 (2H, m), 6.9~7.1 (2H, m), 7.1~7.4 (6H, m), 7.53 (1Hs), 8.34 (1H, d)

HPLC (column: CHIRALCEL OD 4.6 Φ×50 mm. product of Dicell Chemical Industries, KK., elution solvent: n-hexane:isopropyl alcohol=6:1, flow rate;0.8 ml/min).

Retention time: 19.24 min.

PREFERRED EMBODIMENT 4

5-[(3-phenylindolin-1-yl)carbonyl]-4,5,6,7-tetrahydrobenzimidazole hydrochloride (compound 4):

A 100 mg portion of the 5-[(3-phenylindolin-1-yl) carbonyl]-4,5,6,7-tetrahydrobenzimidazole produced in the preferred embodiment 3 was dissolved in 5 ml ethanol, and 0.5 ml of a 4N hydrogen chloride solution in ethyl acetate was added under ice cooling, after which concentration under reduced pressure gave an oily residue. Five ml of acetone was added to precipitate crystals which were collected by filtration. The crystals were dissolved in 1 ml of water and then reconcentrated under reduced pressure and thoroughly dried to obtain the 5-[(3-phenylindolin-1-yl) carbonyl]-4,5,6,7-tetrahydrobenzimidazole hydrochloride (compound 4) listed in the above heading.

$^1$H-NMR (δ ppm, DMSO-d$_6$, 270 MHz): 1.7~1.9 (1H, m), 2.0~2.2 (1H, m), 2.6~2.8 (2H, m), 2.8~3.0 (2H, m), 3.0~3.2 (1H, m), 4.12 (1H, dd), 4.6~4.8 (2H, m), 6.9~7.1 (2H, m), 7.1~7.4 (6H, m), 8.19 (1H, d), 8.87 (1H, s), 14.2 (2H, brs)

PREFERRED EMBODIMENT 5

5-[(3-(3-hydroxyphenyl)indolin-1-yl)carbonyl]-4,5,6,7-tetrahydrobenzimidazole (compound 5):

A mixture of the white powder containing of 3.0 grams of (+)-4,5,6,7-tetrahydrobenzimidazole-5-carboxylic acid hydrochloride obtained in Reference Example 2 and 50 ml of thionyl chloride was refluxed for 2 hours. The reaction solution was concentrated under reduced pressure and the resultant residue was dissolved in 50 ml of chloroform. A 2.71 g portion of the (+)-3-(3-hydroxyphenyl) indoline produced in Reference Example 5 was dissolved in 50 ml of tetrahydrofuran and added to the above-mentioned chloroform solution with stirring under ice cooling. After stirring the reaction solution at room temperature overnight, it was made basic with a saturated, aqueous sodium bicarbonate, solution and was extracted with a chloroform/ethanol mixed solvent. Then the extract solution was dried and concentrated to obtain a white residue. Ethyl acetate was added to the residue and the precipitated crystals were collected by filtration. The crystals were subjected to silica gel column chromatography using a mixed solvent of chloroform:ethanol=10:1 as an eluent to obtain 1.8 g of the 5-[(3-(3-hydroxyphenyl)indolin-1-yl)carbonyl]-4,5,6,7-tetrahydrobenzimidazole (compound 5) listed in the above heading.

$^1$H-NMR (δ ppm, DMSO-d$_6$, 270 MHz): 1.7~1.9 (1H, m). 1.9~2.1 (1H, m), 2.5~2.6 (2H, m), 2.7~2.8 (2H, m), 2.9~3.1 (1H, m), 4.0~4.1 (1H, m), 4.5~4.7 (2H, m), 6.5~6.7 (3H, m), 6.9~7.1 (2H, m), 7.0~7.3 (2H, m). 7.41 (1H, s), 8.21 (1H, d), 9.40 (1H, s), 11.6 (1H, brs)

PREFERRED EMBODIMENT 6

5- [(3-(3-hydroxyphenyl)indolin-1-yl)carbonyl ]-4,5,6,7-tetrahydrobenzimidazole hydrochloride (compound 6):

The same basic procedure as in the preferred embodiment 4 was followed except that the 5-[(3-(3-hydroxyphenyl) indolin-1-yl)carbonyl]-4,5,6,7-tetrahydrobenzimidazole obtained in the preferred embodiment 5 was used instead of 5-[(3-phenylindolin-1-yl)carbonyl]-4,5,6,7-tetrahydrobenzimidazole, to obtain the 5-[(3-(3-hydroxyphenyl)indolin-1-yl)carbonyl]-4,5,6,7-tetrahydrobenzimidazole hydrochloride (compound 6) listed in the above heading.

$^1$H-NMR (δ ppm, DMSO-d$_6$, 270 MHz): 1.7~1.9 (1H, m), 2.0~2.2 (1H, m), 2.6~2.8 (2H, m), 2.8~3.0 (2H, m), 3.0~3.2 (1H, m), 4.0~4.2 (1H, m), 4.5~4.8 (2H, m), 6.5~6.7 (3H, m), 6.9~7.3 (4H, m), 8.18 (1H, d), 8.88 (1H, s), 9.43 (1H, s), 14.1 (2H, brs)

PREFERRED EMBODIMENT 7

5-[(3-(4-hydroxyphenyl)indolin-1-yl)carbonyl]-4,5,6,7-tetrahydrobenzimidazole (compound 7):

The same basic procedure as in the preferred embodiment 5 was followed except that the (+)-3-(4-hydroxyphenyl) indoline obtained in Reference Example 6 was used instead of (+)-3-(3-hydroxyphenyl)indoline, to obtain the 5-[(3-(4-hydroxyphenyl) indolin-1-yl)carbonyl]-4,5,6,7-tetrahydrobenzimidazole (compound 7) listed in the above heading.

$^1$H-NMR (δ ppm, DMSO-d$_6$, 270 MHz): 1.6~1.8 (1H, m), 1.9~2.1 (1H, m), 2.5~2.6 (2H, m), 2.6~2.8 (2H, m), 2.9~3.1 (1H, m), 3.94~4.1 (1H, m), 4.5~4.7 (2H, m), 6.72 (2H, d), 6.9~7.1 (2H, m), 7.02 (2H, d), 7.20 (1H, t), 7.41 (1H, s), 8.19 (1H, d), 9.35 (1H, s), 11.6 (1H, brs)

PREFERRED EMBODIMENT 8

5- [(3-(4-hydroxyphenyl)indolin-1-yl)carbonyl ]-4,5,6,7-tetrahydrobenzimidazole hydrochloride (compound 8):

The same basic procedure as in the preferred embodiment 4 was followed except that the 5-[(3-(4-hydroxyphenyl) indolin-1-yl)carbonyl]-4,5,6,7-tetrahydrobenzimidozole obtained in the preferred embodiment 7 was used instead of 5-[(3-phenylindolin-1-yl)carbonyl]-4,5,6,7-tetrahydrobenzimidazole, to obtain the 5-[(3-(4-hydroxyphenyl)indolin-1-yl)carbonyl]-4,5,6,7-tetrahydrobenzimidazole hydrochloride (compound 8) listed in the above heading.

mp: 155°~258° C.

$[\alpha]_D$=+80.4° (c=1.06, MeOH)

IR (KBr, cm$^{-1}$:1651.6, 1479.5

$^1$H-NMR (δ ppm, DMSO-d$_6$, 270 MHz): 1.74~1.9 (1H, m), 2.0~2.2 (1H, m), 2.64~2.8 (2H, m), 2.8~2.9 (2H, m), 3.0~3.2 (1H, m), 3.94~4.1 (1H, m), 4.5~4.7 (2H, m), 6.73 (2H, d), 6.9~7(4H, m), 7.21 (1H, t), 8.17 (1H, d), 8.88 (1H, s) 9.39 (1H, s), 14.1 (2H, br)

PREFERRED EMBODIMENT 9

5-[(3-(2-hydroxyphenyl)indolin-1-yl)carbonyl]-4,5,6,7-tetrahydrobenzimidazole (compound 9):

The same basic procedure as in the preferred embodiment 5 was followed except that the optically active 3-(2-hydroxyphenyl)indoline obtained in Reference Example 7 was used instead of (+)-3-(3-hydroxyphenyl)indoline, to obtain the 5-[(3-(2-hydroxyphenyl)indolin-1-yl)carbonyl]-4,5,6,7-tetrahydrobenzimidazole (compound 9) listed in the above heading.

$^1$H-NMR (δ ppm, DMSO-d$_6$, 270 MHz): 1.6~1.9 (1H, m), 1.9~2.1 (1H, m), 2.5~2.6 (2H, m), 2.6~2.8 (2H, m), 2,8~3.1 (1H, m), 4.0~4.2 (1H, m), 4.5~4.7 (1H, m), 4.8~5.0 (1H, m), 6.7~7.3 (7H, m), 7.41 (1H, s), 8.20 (1H, d), 9.64 (1H, s), 11.6 (1H, brs)

PREFERRED EMBODIMENT 10

5-[(3-(2-hydroxyphenyl)indolin-1-yl)carbonyl]-4,5,6,7-tetrahydrobenzimidazole hydrochloride (compound 10):

The same basic procedure as in the preferred embodiment 4 was followed except that the 5-[(3-(2-hydroxyphenyl)indolin-1-yl)carbonyl]-4,5,6,7-tetrahydrobenzimidazole obtained in the preferred embodiment 9 was used instead of 5-[(3-phenylindolin-1-yl)carbonyl]-4,5,6,7-tetrahydrobenzimidazole, to obtain the 5-[(3-(2-hydroxyphenyl)indolin-1-yl)carbonyl]-4,5,6,7-tetrahydrobenzimidazole hydrochloride (compound 10) listed in the above heading.

$^1$H-NMR (δ ppm, DMSO-d$_6$, 270 MHz): 1.7~1.9 (1H, m), 2.0~2.2 (1H, m), 2.6~2.8 (2H, m), 2.8~3.0 (2H, m), 3.0~3.2 (1H, m), 4.0~4.2 (1H, m), 4.5~4.7 (1H, m), 4.8~5.0 (1H, m), 6.74 (1H, t), 6.8~7.0 (2H, m), 6.9~7.2 (3H, m), 8.18 (1H, d), 8.89 (1H, s), 9.71 (1H, s), 14.2 (2, brs)

PREFERRED EMBODIMENT 11

5-[(3-(3-methoxyphenyl)indolin-1-yl)carbonyl]-4,5,6,7-tetrahydrobenzimidazole (compound 11):

The same basic procedure as in the preferred embodiment 5 was followed except that the (+)-3-(3-methoxyphenyl)indoline obtained in Reference Example 4 was used instead of (+)-3-(3-hydroxyphenyl)indoline, to obtain the 5-[(3-(3-methoxyphenyl) indolin-1-yl)carbonyl]-4,5,6,7-tetrahydrobenzimidazole (compound 11) listed in the above heading.

$^1$H-NMR (δ ppm, DMSO-d$_6$, 270 MHz): 1,7~1.9 (1H, m), 1.9~2.1 (1H, m), 2.5~2.7 (2H, m), 2.7~2.8 (2H, m), 2.9~3.5 (1H, m), 4.0~4.2 (1H, m), 4.6~4.8 (2H, m), 6.7~6.9 (3H, m), 6.9~7.0 (2H, m), 7.1~7.3 (2H, m), 7.43 (1H, s), 8.21 (1H, d), 11.6 (1H, brs)

PREFERRED EMBODIMENT 12

5-[(3-(3-methoxyphenyl)indolin-1-yl)carbonyl]-4,5,6,7-tetrahydrobenzimidazole hydrochloride (compound 12):

The same basic procedure as in the preferred embodiment 4 was followed except that the 5-[(3-(3-methoxyphenyl)indolin-1-yl)carbonyl]-4,5,6,7-tetrahydrobenzimidazole obtained in the preferred embodiment 11 was used instead of 5-[(3-phenylindolin-1-yl)carbonyl]-4,5,6,7-tetrahydrobenzimidazole, to obtain the 5-[(3-(3-methoxyphenyl)indolin-1-yl)carbonyl]-4,5,6,7-tetrahydrobenzimidazole hydrochloride (compound 12) listed in the above heading.

$^1$H-NMR (δ ppm, DMSO-d$_6$, 270 MHz): 1.7~1.9 (1H, m), 2.0~2.2 (1H, m), 2.6~2.8 (2H, m), 2.8~3.0 (2H, m), 3.0~3.2 (1H, m), 3.73 (3H, s), 4.0~4.2 (1H, m), 4.6~4.8 (2H, m), 6.7~6.9 (3H, m), 6.9~7.1 (2H, m), 7.1~7.3 (2H, m), 8.19 (1H, d), 8.90 (1H, s), 14.2 (2H, brs)

PREFERRED EMBODIMENT 13

5-[(3-phenylindolin-1-yl)carbonyl]-4,5,6,7-tetrahydrobenzimidazole

A mixture of 440 mg of 4,5,6,7-tetrahydrobenzimidazole-5-carboxylic acid hydrochloride (racemic modification) and 2 ml of thionyl chloride was refluxed for 30 minutes. The reaction solution was concentrated under reduced pressure and the resultant residue was dissolved in 3 ml of chloroform. A 0.2 g portion of the (+)- 3-phenylindoline obtained in Reference Example 1 was dissolved in 2 ml of chloroform and added to the abovementioned solution with stirring under ice cooling. After stirring overnight at room temperature, 0.42 ml of triethylamine was added dropwise, and the solution was returned to room temperature and stirred for 2 hours. Saturated sodium bicarbonate aqueous solution was then added to the reaction solution, the reaction mixture was extracted with chloroform. The extract solution was dried and concentrated to obtain a white residue. The residue was purified by silica gel column chromatography to obtain 230 mg of 5-[(3-phenylindolin-1-yl)carbonyl]-4,5,6,7-tetrahydro-benzimidazole as a mixture of two optical isomers.

$^1$H-NMR (δ ppm, CDCl$_3$, 270 MHz): 2.0~2.3 (2H, m), 2.5~3.2 (5H, m), 4.0~4.1 (1H, m), 4.5~4.7 (2H, m), 6.9~7.1 (2H, m), 7.1~7.4 (6H, m), 7.49 (0.5H, s), 7.51 (0.5H, s), 8.84 (1H, d)

HPLC (column; CAPCELL PAK C18 (SG120) 4.6Φ×150 mm, elution solvent; 50 mM aqueous (NH$_4$)$_2$HPO$_4$:MeOH= 1:1, flow rate; 0.8 ml/min, temperature; 35° C.).

Retention times: 33.2 min, 85.7 min.

The above-mentioned 2 optical isomer mixture of 5-[(8-phenylindolin-1-yl) carbonyl]-4,5,6,7-tetrahydrobenzimidazole was subjected to the HPLC described above in small amounts, and the components which eluted out at the slower retention time of 35.7 minutes were collected. The residue obtained by concentration of the eluted solution was dissolved in a mixed solvent of chloroform and ethanol, and after washing with sodium bicarbonate aqueous solution, concentration under reduced pressure gave a yellow residue. Ethyl acetate was added to this residue to precipitate crystals which were collected by filtration.

The abovementioned HPLC and NMR revealed the crystals to be identical to the compound obtained in the preferred embodiment 3.

PREFERRED EMBODIMENT 14

5-[(3-(3-hydroxyphenyl)indolin-1-yl)carbonyl]-4,5,6,7-tetrahydrobenzimidazole hydrochloride The 5-[(3-(3-hydroxyphenyl)indolin-1-yl)carbonyl]-4,5,6,7-tetrahydrobenzimidazole hydrochloride obtained in the preferred embodiment 6 was dissolved in ethanol. The solution was concentrated and the precipitated crystals were collected by filtration. NMR of the crystals revealed them to be identical to the 5-[(3-(3-hydroxyphenyl)indolin-1-yl)carbonyl]-4,5,6,7-tetrahydrobenzimidazole hydrochloride obtained in the preferred embodiment 6, except for containing an equimolar amount of ethanol.

mp: 154.0~193.5° C.

$[\alpha]_D$=+88.1 (c=1.11, MeOH)

IR (KBr, cm$^{-1}$): 1654.8, 1479.8

PREFERRED EMBODIMENT 15

5-[(3-phenylindolin-1-yl)carbonyl]-4,5,6,7-tetrahydrobenziamidazole

One gram of compound 4 obtained in the preferred embodiment 4 was dissolved in ethanol, and the crystals which precipitated upon concentration under reduced pressure were collected by filtration to obtain 0.9 g of 5-[(3-phenylindolin-1-yl) carbonyl]-4,5,6,7-tetrahydrobenziamidazole.

mp: 225.5~234.0° C.

$[\alpha]_D$=+88.0 (c=1.22, MeOH)

HPLC (column; CAPCELL PAK C18 (SG120) 4.6Φ×150 mm, elution solvent; 50 mM aqueous (NH$_4$)$_2$HPO$_4$:MeOH= 1:1, flow rate: 0.8 ml/min, temperature: 5 ° C.).

Retention time: 35.7 min.

IR (KBr, cm$^1$): 1655.7, 1480.3

$^1$H-NMR (δ ppm, DMSO-d$_6$, 270 MHz): 1.7~1.9 (1H, m), 2.0~2.2 (1H, m), 2.6~2.8 (2H, m), 2.8~3.0 (2H, m), 3.0~3.2 (1H, m), 4.12 (1H, dd), 4.6~4.8 (2H, m), 6.9~7.1 (2H, m), 7.1~7.4 (6H, m), 8.19 (1H, d), 8.87 (1H, s), 14.2 (2H, brs)

PREFERRED EMBODIMENT 16

5-[(5-hydroxy-3-phenylindolin-1-yl)carbonyl]-4,5,6,7-tetrahydrobenzimidazole

The same basic procedure as in the preferred embodiment 5 was followed except that the racemic 5-hydroxy-3-phenylindoline was used instead of (+)-3-(3-hydroxyphenyl) indoline, to obtain the compound listed in the above heading.

$^1$H-NMR (δ ppm, DMSO-d$_6$, 270 MHz): 1.6~1.9 (1H, m), 1.9~2.2 (1H, m), 2.5~2.8 (4H, m), 2.8~3.0 (1H, m), 4.0~4.2 (1H, m), 4.5~4.7 (2H, m), 6.33 (1H, s), 6.59 (0.5H, d), 6.60 (0.5H, d), 7.2~7.5 (5H, m), 7.39 (0.5H, s), 7.41 (0.5H, s), 8.02 (1H, d), 9.17 (1H, s), 14.2 (1, brs)

PREFERRED EMBODIMENT 17

5-[(7-hydroxy-3-phenylindolin-1-yl)carbonyl]-4,5,6,7-tetrahydrobenzimidazole

The same basic procedure as in the preferred embodiment 5 was followed except that the racemic 7-hydroxy-3-phenylindoline was used instead of (+)-3-(3-hydroxyphenyl) indoline, to obtain the compound listed in the above heading.

$^1$H-NMR (δ ppm, DMSO-d$_6$, 270 MHz): 1.7~2.0 (1H, m), 2.0~2.3 (1H, m), 2.4~2.8 (4H, m), 3.0~3.3 (1H, m), 4.1~4.3 (1H, m), 4.6~4.8 (2H, m), 6.42 (1H, d), 6.73 (1H, d), 7.01 (1H, d), 7.2~7.5(6H, m), 11.56 (0.5H, s), 11.58 (0.5H, s), 11.6 (1H, brs)

PREFERRED EMBODIMENT 18

5-[(3-(4-fluorophenyl)indolin-1-yl)carbonyl]-4,5,6,7-tetrahydrobenzimidazole

The same basic procedure as in the preferred embodiment 3 was followed except that 3-(4-fluorophenyl)indoline was used instead of (+)-3-phenylindoline, to obtain the compound listed in the above heading.

$^1$H-NMR (δ ppm, CDCl$_3$, 270 MHz): 2.0~2.2 (1H, m), 2.5~3.2 (5H, m), 3.9~4.1 (1H, m), 4.5~4.7 (2H, m), 6.9~7.1 (4H, m), 7.1~7.2 (2H, m), 7.2~7.3 (1H, m), 7.50 (1H, s), 8.34 (1H, d)

PREFERRED EMBODIMENT 19

5-[(3-(3-fluorophenyl)indolin-1-yl)carbonyl]-4,5,6,7-tetrahydrobenzimidazole

The same basic procedure as in the preferred embodiment 3 was followed except that 3-(3-fluorophenyl)indoline was used instead of (+)-3-phenylindoline, to obtain the compound listed in the above heading.

$^1$H-NMR (δ ppm, CDCl$_3$, 270 MHz): 2.0~2.3 (2H, m), 2.5~3.2 (5H, m), 3.9~4.2 (1H, m), 4.5~4.7 (2H, m), 6.8~7.2 (5H, m), 7.2~7.4 (2H, m), 7.49 (1H, s), 8.34 (1H, d)

PREFERRED EMBODIMENT 20

5-[(7-fluoro-3-phenylindolin-1-yl)carbonyl]-4,5,6,7-tetrahydrobenzimidazole

The same basic procedure as in the preferred embodiment 1 was followed except that 7-fluoro-3-phenylindoline (racemic modification) was used instead of 3-phenylindoline (racemic modification), to obtain the compound listed in the above heading.

$^1$H-NMR (δ ppm, CDCl$_3$, 270 MHz): 1.9~2.3 (2H, m), 2.6~3.2 (5H, m), 4.0~4.2 (1H, m), 4.4~4.7 (2H, m), 6.8~6.9 (1H, m), 6.9~7.1 (2H, m), 7.1~7.2 (2H, m), 7.2~7.4 (3H, m), 7.49 (0.5H, s), 7.50 (0.5H, s)

PREFERRED EMBODIMENT 21

5-[(5-fluoro-3-phenylindolin-1-yl)carbonyl]-4,5,6,7-tetrahydrobenzimidazole

The same basic procedure as in the preferred embodiment 1 was followed except that 5-fluoro-3-phenylindoline (racemic modification) was used instead of 3-phenylindoline (racemic modification), to obtain the compound listed in the above heading.

$^1$H-NMR (δ ppm, CDCl$_3$, 270 MHz): 1.9~2.3 (2H, m), 2.5~3.2 (5H, m), 4.0~4.2 (1H, m), 4.5~4.7 (2H, m), 6.6~6.8 (1H, m), 6.9~7.0 (1H, m), 7.1~7.2 (2H, m), 7.2~7.4 (3H, m), 7.48 (0.5H, s), 7.50 (0.5H, s), 8.30 (1H, m)

The pharmacological effects of the compounds of the invention are demonstrated below. The compounds of the invention used were an isomeric mixture of 5-[(3-phenylindolin-1-yl)carbonyl]-4,5,6,7-tetrahydrobenzimidazole hydrochloride (the compound listed in the preferred embodiment 2, hereunder referred to as "compound 2") and an optically active form thereof (the compound listed in the preferred embodiment 4, hereunder referred to as "compound 4"), 5-[(3-(3-hydroxyphenyl) indolin-1-yl)carbonyl]-4,5,6,7-tetrahydrobenzimidazole hydrochloride (the compound listed in the preferred embodiment 6, hereunder referred to as "compound 6"), 5-[(3-(4-hydroxyphenyl)indolin-1-yl)carbonyl]- 4,5,6,7-tetrahydrobenzimidazole hydrochloride (the compound listed in the preferred embodiment 8, hereunder referred to as compound 8). 5-[(3-(2-hydroxyphenyl)indolin-1-yl) carbonyl]-4,5,6,7-tetrahydrobenzimidazole hydrochloride (the compound listed in the preferred embodiment 10, hereunder referred to as "compound 10"), and 5-[(3-(3- methoxyphenyl)indolin-1-yl)carbonyl]-4,5,6,7-tetrahydrobenzimidazole (the compound listed in the preferred embodiment 12, hereunder referred to as "compound 12").

For comparison there are also provided the results of tests conducted by the same method on Ondansetron and the following compounds:

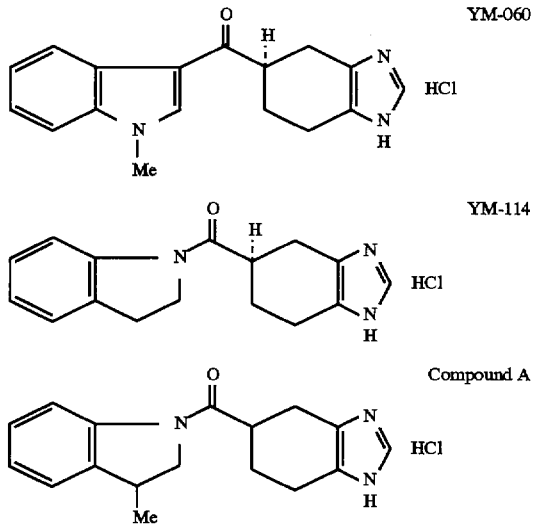

described in Japanese laid-open patent publication No. Hei-3-223278.

TEST 1

Intestinal 5-HT$_3$ receptor antagonism

The test was conducted following the method of Miyata, et al. (The Journal of Pharmacology and Experimental Therapeutics Vol.259, No:1, 15 (1991)).

Male Hartley guinea pigs with a body weight of 300–400 g were bled to death, the distal colon (3–10 cm from the anus) was isolated and suspended in a Magnus tube filled with Krebs solution aerated with a mixed gas (95% $O_2$, 5% $CO_2$), and subjected to a tensile load of 1 g. After constant contraction by cumulative addition of 2-methylserotonin ($10^{-6}$–$10^{-4}$ M) was obtained, the test agent was added and the pA$_2$ value of the test agent was calculated based on its inhibiting action on the initial value.

The value (pA$_2$ value) is defined as the negative logarithm (–logM) of the molar concentration (M) of the antagonist required to reduce the effect of serotonin at a concentration of 2 times the 2-methylserotonin concentration (EC$_{50}$) necessary to induce half of the maximum contraction reaction, to an effect induced by an EC50 of serotonin.

TABLE 1

| Test compound | pA$_2$ | M (×$10^{-9}$ Mole) |
|---|---|---|
| Ondansetron | 6.6 | 227 |
| YM-060 | 8.4 | 4.5 |
| YM-114 | 8.4 | 4.0 |
| Compound - A | <8.0 | |
| Compound - 2 | 9.0 | 1.0 |
| Compound - 4 | 9.6 | 0.30 |
| Compound - 6 | 10.0 | 0.09 |
| Compound - 8 | 10.0 | 0.11 |
| Compound - 10 | 9.9 | 0.05 |
| Compound - 12 | 10.0 | 0.13 |

As is clear from Table 1, the compounds of the invention exhibited a strong antagonism against 5-HT$_3$ receptors in the colon of the lower intestinal tract, which effect was unpredictable based on the activity of known compounds with relatively similar structures. Compound 4 had about 15-fold activity in the colon compared to YM-060 and YM-114.

TEST 2

Antagonism against 5-HT-induced intestinal secretion:

This test was conducted following the method of Oe, et al. (Folia pharmacologica Japonica, Vol.101, 299 (1993)). Male wister rats (8–11 weeks old) were anesthetized with urethane, and the abdomen was opened a polyethylene catheter was placed in the jejunum 5 cm distal to the duodenojejunal flexure and fixed by ligation. The second ligation was made at a distal point of 20 cm to create a jejunal loop. Two ml of physiological saline was injected into this loop and initiated continuous injection of physiological saline (0.1 ml/min) or 5-HT (3 μg/0.1 ml/kg/min, serotonin treated group) into the mesenteric artery through the mesenteric artery gastric branch, and after 30 minutes the jejunal loop was isolated, the residual fluid amount was measured, and the net fluid transfer per gram of tissue weight was calculated. The net fluid transfer was expressed as the fluid amount (weight) change in 30 minutes per jejunal tissue weight (g/30 min/g). A "+" was assigned when the fluid amount increased compared with 2 ml of physiological saline injected into the loop, and "–" when it decreased

TABLE 2

| | net fluid transfer in jejunal loop (g/30 min/g tissue weight) |
|---|---|
| physiological saline-administered group (control group) | –0.71 ± 0.06 |
| serotonin treated group | –0.52 ± 0.06 |

As shown in Table 2, serotonin administration produced an acceleration in intestinal secretion of 0.19 g/30 min/g tissue weight.

Next, compound 4 (0.1 or 1 μg/ml) or YM-060 (1 or 10 μg/ml) was administered via the caudal vein 15 minutes prior to initiating continuous administration of serotonin, to examine the influence on the intestinal secretion-accelerating effect of serotonin.

TABLE 3

| Drug | Dosage (μg/kg) | net fluid transfer in jejunal loop (g/30 min/g tissue weight) | No. of tests |
|---|---|---|---|
| Compound-4 | 0.1 | –0.50 ± 0.07 | 5 |
| | 1.0 | –0.80 ± 0.09 | 6 |
| YM-060 | 1.0 | –0.49 ± 0.06 | 5 |
| | 10 | –0.74 ± 0.09 | 3 |

As is clear from Table 3, the compound of the present invention also has stronger antagonism against 5-HT$_3$ receptors in the upper intestine compared to the comparison compound.

TEST 3

Inhibiting effect on restrained stress-induced diarrhea (oral administration):

This test was conducted following the method of Miyata, et al. (The Journal of Pharmacology and Experimental Therapeutics Vol.261, No. 1, 297 (1992)). Nine-week-old male Wistar rats fasted overnight were placed in a stress cage and their feces produced in 5 hours were observed. Of 15 rats, 14 developed diarrhea. The inhibiting effect on diarrhea was measured by oral administration of the test compounds one hour prior to placement in the stress cage. Table 4 shows the results of Test 3 on compounds 4, 6 and 8 and on the comparison compounds which exhibited relatively high colonic 5-$HT_3$ receptor antagonism activity ($pA_2>8.0$) in Test 1.

TABLE 4

| Test compound | Dosage | No. of animals with diarrhea/ No. of animals used | Inhibition rate |
|---|---|---|---|
| YM-060 | 30 µg/kg | 4/10 | 60% |
| YM-060 | 100 µg/kg | 2/8 | 75% |
| YM-114 | 30 µg/kg | 7/10 | 30% |
| Compound-4 | 30 µg/kg | 3/10 | 70% |
| Compound-6 | 100 µg/kg | 0/5 | 100% |
| Compound-8 | 30 µg/kg | 2/10 | 70% |

TEST 4

Inhibiting effect on restraint stress-induced diarrhea (intraabdominal administration):

This test was conducted in the same manner as Test 3. Nine- to ten-week-old male Wistar rats fasted overnight were placed in a stress case and their feces produced in 5 hours were observed. Of 15 rats, 14 developed diarrhea. The inhibiting effect on diarrhea was measured by intraabdominal administration of a test compound 30 minutes prior to placement in the stress cage. Table 5 shows the results of Test 4 on YM-060 and compound 4.

TABLE 5

| Test compound | Dosage | No. of animals with diarrhea/ No. of animals used | Inhibition rate |
|---|---|---|---|
| YM-060 | 30 µg/kg | 7/14 | 50% |
| Compound-4 | 30 µg/kg | 1/10 | 90% |

Tables 4 and 5 demonstrate that the compounds of the invention exhibit a very strong antidiarrheal effect.

TEST 5

Inhibiting effect on duodenal extension reflex:

Unfasted male Wistar rats with a body weight of 300–390 g were opened at the abdomen under urethane anesthesia, and ligated at 2 locations, the gastric pyloric region and 3–4 cm directly under it, to create a duodenal loop. One end of a vinyl catheter with an inner diameter of 5 mm, the other end of which was connected to a open-bottomed beaker, was inserted from the anal end of the loop, and the loop, tube and beaker were filled with physiological saline. The beaker was raised at once to create a internal loop pressure of 75 cm $H_2$, and the depressor reflex and effect of the test agent administration were observed. First, an extension stimulus was applied at intervals of 10 minutes and an initial value was recorded after constant depressor reflex was obtained. The test agent was then administrated intravenously, and at 5, 15 and 25 minutes after administration an extension stimulus was applied, the depressor reflex was observed, and the differences were expressed as percentages with respect to the initial value, to give the inhibition rates.

TABLE 6

| Test agent | Dosage (µg/kg) | Inhibition rate | | |
|---|---|---|---|---|
| | | 5-min value | 15-min value | 25-min value |
| Compound-4 | 1 | 21.7(6)* | 6.7(6) | 20.2(6) |
| | 10 | 16.3(7) | 17.8(7) | 21.1(7) |
| YM-060 | 1 | −27.9(5) | −30.8(5) | −14.8(5) |
| | 10 | 16.3(6) | 6.3(6) | 7.9(5) |
| Tropisetron | 10 | 42.7(5) | 44.1(5) | 30.6(5) |

*Number of tests in parentheses

As is clear from Table 6. compound 4 inhibited intestinal sensitivity to dilatation stimulation more strongly than YM-060.

TEST 6

Antagonism against Von Bezold-Jarisch reflex (BJ reflex):

This test was conducted following the method of Cohen. at al. (The Journal of Pharmacology and Experimental Therapeutics Vol.248, No. 1, 197 (1989)). Male SD rats with a body weight of around 300 g were anesthetized by intraabdominal administration of 1.25 g/kg urethane, and an intravenous injection cannule was inserted in the right femoral vein while a sphygmomanometric cannule was inserted into the left femoral artery. The pulse was determined by measuring the electrocardiogram R waves (secondary induction) with an instantaneous pulse rate meter. After confirming satisfactory reproducibility of the reflexive bradycardia induced by intravenous administration of 30 µg/kg serotonin, the test compounds were intravenously administered 5 minutes prior to serotonin administration, the inhibition rates with respect to the initial values were found and the 50% inhibition doses ($ID_{50}$) were calculated. Table 7 shows the results of Test 6 on the compounds which exhibited relatively high colonic 5-$HT_3$ receptor antagonism activity ($pA_2>8.0$) in Test 1.

TABLE 7

| Test compound | $ID_{50}$ (µg/kg) | $ID_{50}$ (nmole/kg)) |
|---|---|---|
| YM-060 | 0.026 | 0.086 |
| YM-114 | 0.15 | |
| Compound - 2 | 0.30 | |
| Compound - 4 | 0.15 | 0.39 |
| Compound - 6 | 0.15 | |
| Compound - 8 | 0.13 | |

It is clear from Table 7 that the compounds of the invention also have stronger antagonism against 5-$HT_3$ receptors in the heart.

TEST 7

Duration action:

The BJ reflex inhibition was measured in the same basic manner as in Test 6. However, serotonin was administered first at 5 minutes and then every 30 minutes thereafter subsequent to intravenous administration of the test compounds (1 µg/kg), the BJ reflex was measured, and the inhibition rates with respect to the initial values were calculated and used as the indexes of duration of action. FIG. 1 shows the results of Test 7 for compound 4 and the comparison compounds which exhibited relatively high intestinal 5-$HT_3$ receptor antagonism activity ($pA_2>8.0$) in Test 1.

As is clear from FIG. 1, the compound of the invention was also highly superior to the comparison compounds in terms of duration of action.

TEST 8

Inhibiting effect on cisplatin-induced vomiting:

Vomiting was induced in ferrets by administration of cisplatin. The inhibiting effect on this vomiting was observed. The vomiting reaction was observed for 6 hours after administration of the cisplatin. The test agents were orally administered one hour prior to cisplatin administration. The ferrets used in the test had a body weight of 1.0–1.5 kg. The test results for compound 4 and YM-060 are provided below.

TABLE 8

| | Dosage µg | No. of vomiting animals/ No. of animals used | No. of vomitings | No. of retching | Latency* (min) | Latency** (min) |
|---|---|---|---|---|---|---|
| Control | | 4/4 | 7.0 | 116.3 | 100.0 | 169.8 |
| Compound-4 | 0.3 | 2/2 | 7.0 | 139.0 | 114.0 | 114.0 |
| | 1.0 | 1/3 | 1.0 | 14.7 | >289.7 | 293.0 |
| YM-060 | 0.3 | 2/2 | 6.5 | 126.0 | 127.0 | 134.0 |
| | 1.0 | 3/5 | 1.2 | 41.6 | >272.2 | >303.0 |

Latency*: time to initial retching
Latency**: time to initial vomiting

YM-060 is known to have a powerful antiemetic effect (The Japanese Journal of Pharmacology. 57, 387–395 (1991)), and compound 4 exhibited a similar antiemetic effect as YM-060.

TEST 9

Accelerating effect on gastric emptying

Seven-week-old male SD rats which had been fasted for 24 hours were used. The effect on gastric emptying was studied in rats with reduced gastric emptying due to cisplatin. The rats were intragastrically administered the test feed (1.5% aqueous CMC solution containing 50 mg/100 ml phenol red) at 1.5 ml/rat, and after 15 minutes the stomachs were dissected, the residual amount of phenol red in the stomach was measured, in order to determine the gastric emptying in normal animals. A cisplatin-induced reduction in gastric emptying was measured by intraabdominal administration of cisplatin (10 mg/kg) 30 minutes prior to supplying the test feed. The test compound was also administered orally 30 minutes prior to the cisplatin administration to study the accelerating effect of the test compound on gastric emptying.

TABLE 9

| | Gastric evacuation (%) | |
|---|---|---|
| Group | Compound 4 | YM-060 |
| 0.3 µg/kg group | 73.3 | 51.8 |
| 1.0 µg/kg group | 82.4 | 74.2 |
| Normal | | 71.0 |
| Control (cisplatin-administered) | | 26.8 |

As is clear from the results shown in Table 9, compound 4 inhibited similar cisplatin-induced gastric emptying reduction at 0.3 µg/kg, or less than ⅓ the amount of YM-060, and gastric emptying was further accelerated at a dose of 1.0 µg/kg.

TEST 10

Toxicity:

The acute toxicity values ($LD_{50}$) for compounds 4, 6 and 8 in rats were 1000 mg/kg or higher with oral administration, and there were no cases of death at 1000 mg/kg. The results in Test 10 suggest that the compounds of the present invention are adequately safe as drugs.

INDUSTRIAL APPLICABILITY

Thus, the compounds of the present invention not only exhibit the same effect as known 5-$HT_3$ receptor antagonists, but also have more powerful intestinal 5-HT3 receptor antagonism than known 5-HT3 receptor antagonists, as well as a more powerful antidiarrheal effect and greater alleviation of abdominal pain, while also having excellent duration of action and gastric emptying-accelerating effect; they are hence useful as prophylactic or therapeutic agents against irritancy or vomiting induced by chemotherapy or radiation, reflux esophagitis, gastritis, migraine, combined, neuralgia, anxiety, psychosis, schizophrenia, memory disturbance, amnesia, dementia, rider's vertigo, arrhythmia, postoperative irritancy or vomiting, alcohol-, nicotine-or narcotic-dependency, pruritus, etc., and are particularly useful as prophylactic or therapeutic agents against irritable bowel syndrome, stress-related diarrhea, intestinal trauma-related diarrhea, radiation-induced diarrhea, antitumor agent-induced diarrhea, accelerated defecation, constipation, gastrointestinal motor disturbance and enteritis, as well as the abdominal pain accompanying the above.

We claim:

1. An indoline compound represented by the following formula:

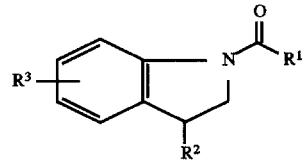

wherein $R^1$ represents the group

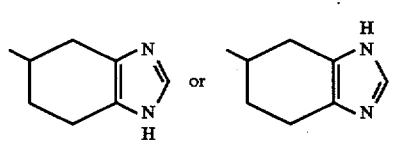

$R^2$ represents a phenyl group which is substituted unsubstituted or an aromatic heterocyclic group, and $R^3$ represents hydrogen, a halogen, or a lower alkyl group, hydroxyl group, lower alkoxy group, carbamoyl group or lower alkoxycarbonyl group;

or a physiologically acceptable salt or solvate of the compound.

2. An indoline compound according to claim 1 wherein $R^2$ is a phenyl group which is unsubstituted or substituted and $R^3$ is hydrogen.

3. An indoline compound according to claim 1, being 5-[(3-phenylindolin-1-yl)carbonyl]-4,5,6,7-tetrahydrobenzimidazole, or a physiologically acceptable salt or solvate thereof.

4. An indoline compound according to claim 1, being 5-[(3-(2-hydroxyphenyl)indolin-1-yl)carbonyl]-4,5,6,7-tetrahydrobenzimidazole, or a physiologically acceptable salt or solvate thereof.

5. An indoline compound according to claim 1, being 5-[(3-(3-hydroxyphenyl)indolin-1-yl)carbonyl]-4,5,6,7-tetrahydrobenzimidazole, or a physiologically acceptable salt or solvate thereof.

6. An indoline compound according to claim 1, being 5-[(3-(4-hydroxyphenyl)indolin-1-yl)carbonyl]-4,5,6,7-tetrahydrobenzimidazole, or a physiologically acceptable salt or solvate thereof.

7. An indoline compound according to claim 1, being 5-[(3-(3-methoxyphenyl)indolin-1-yl)carbonyl]-4,5,6,7-tetrahydrobenzimidazole, or a physiologically acceptable salt or solvate thereof.

8. A pharmaceutical composition, comprising:
a physiologically acceptable additive, and an effective 5-HT$_3$ receptor antagonist amount of an indoline compound of the following formula:

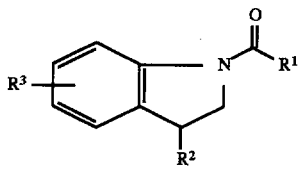

wherein R$^1$ represents the group

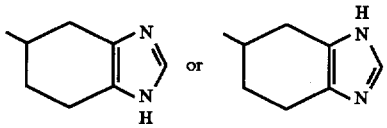

R$^2$ represents a phenyl group which is substituted or unsubstituted or an aromatic heterocyclic group, and R$^3$ represents hydrogen, a halogen, or a lower alkyl group, hydroxyl group, lower alkoxy group, carbamoyl group or lower alkoxycarbonyl group;

or a physiologically acceptable salt or solvate of the compound.

9. A pharmaceutical composition according to claim 8, wherein R$^2$ is a phenyl group which may be substituted and R$^3$ is hydrogen.

10. A pharmaceutical composition according to claim 8, said idoline compound being, 5-[(3-phenylindolin-1-yl)carbonyl]-4,5,6,7-tetrahydrobenzimidazole, or a physiologically acceptable salt or solvate thereof.

11. A pharmaceutical composition according to claim 8, said indoline compound being 5-[(3-(2-hydroxyphenyl)indolin-1-yl)carbonyl]-4,5,6,7-tetrahydrobenzimidazole, or a physiologically acceptable salt or solvate thereof.

12. A pharmaceutical composition according to claim 8, said incoline compound being 5-[(3-(3-hydroxyphenyl)indolin-1-yl)carbonyl]-4,5,6,7-tetrahydrobenzimidazole, or a physiologically acceptable salt or solvate thereof.

13. A pharmaceutical composition according to claim 8, said indoline compound being 5-[(3-(4-hydroxyphenyl)indolin-1-yl)carbonyl]-4,5,6,7-tetrahydrobenzimidazole, or a physiologically acceptable salt or solvate thereof.

14. A pharmaceutical composition according to claim 8, said indoline compound being 5-[(3-(3-methoxyphenyl)indolin-1-yl)carbonyl]-4,5,6,7-tetrahydrobenzimidazole, or a physiologically acceptable salt or solvate thereof.

15. A pharmaceutical composition according to claim 8 which is a prophylactic or therapeutic agent against irritancy or vomiting induced by chemotherapy or radiation, reflux esophagitis, gastritis, migraine, compound headache, neuralgia, anxiety, insanity, schizophrenia, memory disturbance, amnesia, dementia, rider's vertigo, arrhythmia, postoperative irritancy or vomiting, alcohol-, nicotine-or narcotic-dependency, or pruritus.

16. A method of treating a mammal for a condition responsive to 5-HT$_3$ receptor antagonists, comprising administering to the mammal an effective prophylactic or therapeutic amount of an indole compound of the following formula:

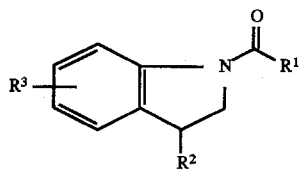

wherein R$^1$ represents the group

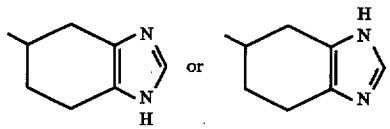

R$^2$ represents a phenyl group which is substituted or unsubstituted or an aromatic heterocyclic group, and R$^3$ represents hydrogen, a halogen, or a lower alkyl group, hydroxyl group, lower alkoxy group, carbamoyl group or lower alkoxycarbonyl group;

or a physiologically acceptable salt or solvate of the compound.

17. A method according to claim 16, wherein R$^2$ is a phenyl group which is substituted or unsubstituted and R$^3$ is hydrogen.

18. A method according to claim 16, comprising administering 5-[(3-phenylindolin-1-yl)carbonyl]-4,5,6,7-tetrahydrobenzimidazole, or a physiologically acceptable salt or solvate thereof.

19. A method according to claim 16, comprising administering 5-[(3-(2-hydroxyphenyl)indolin-1-yl)carbonyl]-4,5,6,7-tetrahydrobenzimidazole, or a physiologically acceptable salt or solvate thereof.

20. A method according to claim 16, comprising administering 5-[(3-(3-hydroxyphenyl)indolin-1-yl)carbonyl]-4,5,6,7-tetrahydrobenzimidazole, or a physiologically acceptable salt or solvate thereof.

21. A method according to claim 16, comprising administering 5-[(3-(4-hydroxyphenyl)indolin-1-yl)carbonyl]-4,5,6,7-tetrahydrobenzimidazole, or a physiologically acceptable salt or solvate thereof.

22. A method according to claim 16, comprising administering 5-[(3-(3-methoxyphenyl)indolin-1-yl)carbonyl]-4,5,6,7-tetrahydrobenzimidazole, or a physiologically acceptable salt or solvate thereof.

23. A method according to claim 16, wherein said condition is selected from irritable bowel syndrome, stress-related diarrhea, intestinal trauma-related diarrhea, radiation-induced diarrhea, antitumor agent-induced diarrhea, accelerated defecation, constipation, gastrointesti nal motor disturbance, enteritis, and abdominal pain accompanying the above.

24. A method according to claim 16, wherein said condition is diarrhea.

25. A method according to claim 16, wherein said condition is irritable bowel syndrome.

26. A method according to claim 16, wherein said condition is constipation.

27. A method according to claim 16, wherein said condition is vomiting.

28. A method according to claim 16 wherein said condition is vomitting or irritancy induced by chemotherapy or radiation, reflux esophagitis, gastritis, migraine, compound headache, neuralgia, anxiety, insanity, schizophrenia, memory disturbance, amnesia, dementia, rider's vertigo, arrhythmia, postoperative irritancy or vomiting, alcohol-, nicotine-or narcotic-dependency, or pruritus.

* * * * *